United States Patent [19]

Graf et al.

[11] Patent Number: 4,814,513

[45] Date of Patent: Mar. 21, 1989

[54] PREPARATION OF CARBONYL COMPOUNDS

[75] Inventors: Fritz Graf, Speyer; Heinz Engelbach, Limburgerhof; Leopold Hupfer, Friedelsheim; Harald Schultheiss, Frankenthal; Michael J. Sprague, Mannheim, all of Fed. Rep. of Germany

[73] Assignee: BASF Aktiengesellschaft, Ludwigshafen, Fed. Rep. of Germany

[21] Appl. No.: 130,687

[22] Filed: Dec. 9, 1987

[30] Foreign Application Priority Data

Dec. 19, 1986 [DE] Fed. Rep. of Germany ....... 3643469

[51] Int. Cl.$^4$ ............................................. C07C 45/38
[52] U.S. Cl. .................................. 568/471; 568/470; 568/472; 568/473
[58] Field of Search ................ 568/470, 471, 472, 473

[56] References Cited

U.S. PATENT DOCUMENTS

| | | | |
|---|---|---|---|
| 3,948,997 | 4/1976 | Howe et al. | 568/471 |
| 4,242,282 | 12/1980 | Diem et al. | 568/471 |
| 4,258,216 | 3/1981 | Treck et al. | 56/473 |
| 4,282,374 | 8/1981 | Engelbach et al. | 568/471 |
| 4,503,261 | 3/1985 | Sauer et al. | 568/471 |
| 4,555,583 | 11/1985 | Toyoda et al. | 568/473 |

OTHER PUBLICATIONS

Patent Abstracts of Japan, Unexamined applications, C. Field, vol. 9, No. 241, 27 Sep. 1985, p. 97, C-306.

*Primary Examiner*—Werren B. Lone
*Attorney, Agent, or Firm*—John H. Shurtleff

[57] ABSTRACT

A process for the preparation of carbonyl compounds by oxidation of alcohols in the gas phase with a gas containing oxygen in the presence of catalysts containing copper or silver and a phosphorus compound that is volatile under the conditions of the reaction, the ratio of the mass of phosphorus to the mass of the alcohol being less than 0.5 ppm.

10 Claims, No Drawings

PREPARATION OF CARBONYL COMPOUNDS

The present invention relates to a novel process for the preparation of carbonyl compounds by oxidation of alcohols in the gas phase by means of a gas containing oxygen in the presence of catalysts containing copper or silver or both copper and silver.

From German Pat. No. 19 23 048 it is known that glyoxal can be prepared by oxidation of ethylene glycol in the gas phase with an oxidation catalyst containing copper in combination with tin, phosphorus, arsenic, antimony, or bismuth. The catalyst, which can also contain silver, is employed as an alloy, preferably in the form of turnings or gauze. With the combination silver/copper/phosphorus yields are said to be 55–72%, based on converted ethylene oxide, but the higher values can only be achieved at the expense of incomplete conversion of the glycol. This is unsatisfactory from the economic point of view, since the residual glycol can only be removed from the product at great expense. Moreover, this known process affords inadequate space-time yields. A further disadvantage is the troublesome preparation of the catalyst.

In German Pat. No. 19 67 147 a silver catalyst containing phosphorus is proposed for the preparation of glyoxal from ethylene glycol. With this process too glyoxal yields of up to 70%, based on converted ethylene glycol, are obtained at the expense of unsatisfactory conversion. Space-time yields are also unsatisfactory.

According to German Laid-Open Application No 21 58 343 the selectivity of the catalysts described in German Pat. No. 19 23 048 falls from 60–64% initially to 55% after 700 h of service. It is also stated that a catalyst containing copper, silver, and phosphorus can be regenerated after 700 h of service by reduction for 12 h at 450° C. German Laid-Open Applicaton 21 58 344 describes the regeneration of a catalyst containing copper and phosphorus: oxygen in excess is passed over the catayst for at least one day. These regeneration processes have the disadvantages that they involve loss of production and require elaborate safety precautions to ensure that the air used for regeneration cannot mix with reaction gas.

Oxidation of ethylene glycol in the gas phase over copper catalysts or a catalyst bed containing copper and silver crystals in accordance with the processes of U.S. Pat. No. 4,282,374 and U.S. Pat. No. 4,503,261 gives results that are advantageous with respect to the life of the catalysts and the glyoxal yields if the reaction is carried out in the presence of a volatile phosphorus compound, the ratio of the mass of phosphorus to the mass of ethylene glycol being from 1 to 100 ppm or from 0.5 to 20 ppm. However, after prolonged operation by theseprocesses it has emerged that the glyoxal yield and the purity of the product deteriorate increasingly with the duration of the trial. This disadvantage is to be attributed to the increased formation of formaldehyde and carbon monoxide and dioxide.

The presence of formaldehyde in glyoxal is highly undesirable for many applications, on account of the toxicological properties of formaldehyde and its high reactivity. Since formaldehyde can only be removed from the crude glyoxal with considerable effort and at the expense of loss of yield, say, by treatment with steam or by chemical reaction, it was necessary to seek a process that would allow the preparation of glyoxal by catalytic oxidation of ethylene glycol in the gas phase over long periods of operation largely without the formation of interfering side products.

We have found that the preparation of carbonyl compounds of the general formula I—where $R^1$ is a hydrogen atom and $R^2$ is the group $OR^5$ or $R^1$ and $R^2$ together are an oxygen atom, $R^3$ is a hydrogen atom, alkyl of 1-8 carbon atoms, or cycloalkyl, $R^4$ is a hydrogen atom or alkyl of 1-3 carbon atoms, and $R^5$ is alkyl of 1-4 carbon atoms, cycloalkyl, or alkoxyalkyl that may include a keto or an aldehyde group—from alcohols of the general formula II—where $R^3$ and $R^4$ are as stated above and $R^6$ is a hydrogen atom, alkyl or hydroxyalkyl of 1-4 carbon atoms, cycloalkyl, or alkoxyalkyl that may carry a hydroxyl group—by oxidation in the gas phase with a gas containing oxygen, in the presence of catalysts containing copper or silver and a phosphorus compound that is volatile under the conditions of the reaction, can be performed particularly advantageously if the ratio of the mass of the phosphorus to the mass of the alcohol is less than 0.5 ppm.

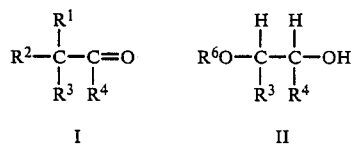

By the novel process, in which the ratio of the mass of phosphorus to the mass of alcohol is restricted to values below 0.5 ppm, glyoxal is obtained from ethylene glycol, for instance, in high yield and purity even in sustained operation. This advantageous result is unexpected, since according to the statement in U.S. Pat. No. 4,503,261 (column 3, ll. 54–61) it is necessary for the ratio of the mass of phosphorus to the mass of ethylene glycol to lie between 0.5 ppm and 20 ppm, to suppress the formation of carbon dioxide on the one hand and on to the other to avoid affecting the activity of the catalyst.

In the alcohols of general formula II alkyl means methyl, ethyl, propyl, or butyl, for instance, and cycloalkyl means cyclohexyl or cyclopentyl, for instance. Alkoxyalkyl that may carry a hydroxyl group includes $HOCH_2CH_2OCH_2CH_2-$, for instance. In the novel process aldehyde groups are formed at the sites of terminal hydroxyl groups, and keto groups are formed at the sites of secondary hydroxyl groups.

The following are examples of starting compounds of general formula II:

$HOCH_2CH_2OH$   $CH_3OCH_2CH_2OH$   $C_2H_5OCH_2CH_2OH$ $CH_3CH(OH)CH_2OH$   $C_2H_5CH(OH)CH_2OH$

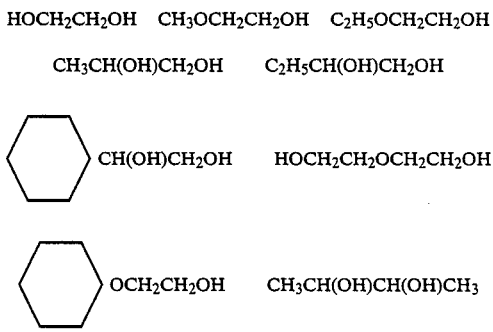

Oxidation of the alcohol in the gas phase with a gas containing oxygen over catalysts containing copper, or silver, or both is carried out in the manner that is itself known, for instance at temperatures between about 225° C. and about 500° C. Metallic copper or silver, copper or silver alloys, or compounds with metals or non-metals are suitable as catalysts; examples are copper phosphides, copper bronzes or alloys with silver, or gold, or both, copper ores such as malachite and copper or silver compounds that during the reaction can be completely or partly reduced to copper or silver, such a copper(I) oxide, silver(I) oxide, and copper(III) oxide, and compounds that form copper oxides when heated, such as copper nitrate and copper acetate. Copper phosphate and copper antimonate are also suitable. Oxides of non-metals and other metals can be mixed with the copper compounds, e.g. oxides of zinc, chromium, phosphorus, antimony, tin, or bismuth. The catalystcontaining copper or silver can be applied to an inert carrier or if necessary diluted with inert material. The catalyst can also be subjected to reducing treatment before use, if required.

Catalysts that do not have a large internal surface are preferred, for instance those with specific surfaces less than 50 $m^2/g$. Metallic copper or silver and alloys containing substantial proportions of copper or silver are of special interest industrially. They are used in the form of turnings, wire mesh, or gauze, or applied to carriers, for instance on an inert carrier of low specific surface.

It is expedient to use phosphorus compounds that vaporize without decomposition and do not react with components of the synthesis gas under the conditions of the process as the phosphorus compound that is volatile under the conditions of the reaction. These include, for instance, esters of phosphoric acid, phosphorous acid, or phosphonic acids, such as trimethyl phosphate, triethyl phosphate, triisopropyl phosphate, tri-n-propyl phosphate trimethyl phosphite, triethyl phosphite, triethylphosphine oxide, diethyl methylphosphonate, dimethyl methylphosphonate, and diethyl ethylphosphonate. In accordance with the invention the amounts of the phosphorus compounds employed are such that the ratio of the mass of phosphorus to the mass of the alcohol is less than 0.5 ppm. Preferably this ratio is 0.05–0.48 ppm.

The process can be carried out in the following way, for example: a gaseous mixture of the alcohol and water (0.1–99% water) together with oxygen (about 0.5 to 2.0 moles per mole of alcohol) and, possibly, nitrogen (0–99% of the volume of the whole gas mixture) is passed over the catalyst, which is maintained at 225°–500° C., after the volatile phosphorus compound has been introduced into the initial gas mixture. As usual the gaseous reaction mixture is scrubbed with water when it leaves the reactor. In order to obtain better control of the traces of phosphorus to be added it may be expedient to dissolve the phosphorus compound in water or the alcohol and meter the solution into the stream of hot synthesis gas.

The glyoxal obtained from ethylene glycol by the novel process, which can be obtained direct as the 40% aqueous solution of commerce, is notable for its high purity, which is unchanged even after long periods of operation. Thus the 40% glyoxal solution contains less than 0.2% of unreacted glycol; the glycolaldehyde content is about 0.1% and the formaldehyde content lies around 0.5%.

EXAMPLE 1

Copper packing (123 parts) is so placed in a stainless-steel tube reactor of internal diameter 20 mm that the height of the catalyst filling is 30 cm. A synthesis gas mixture consisting of ethylene glycol (12 parts by weight), air (27 parts by volume), and nitrogen (100 parts by volume) is passed through the tube reactor each hour. Phosphorus (0.3 ppm of the mass of ethylene glycol) is added to the synthesis gas in the form of trimethyl phosphate. The reaction is carried out at a temperature of 360° C. After leaving the reactor the reaction gas is brought into contact with water and the products of the reaction are dissolved in the aqueous phase.

The glyoxal yield is 77.1%, based on the amount of ethylene glycol employed. Formaldehyde is formed to the extent of 0.6%. Combustion to carbon monoxide and dioxide amounts to 15.5%. A further side product is glycolaldehyde, with a yield of 1.0%. After operation for 15 days the glyoxal yield is 79.3%;the yields of formaldehyde, carbon oxides, and glycolaldehyde are found to be 0.5%, 16.3%, and 0.5% respectively.

EXAMPLE 2

The procedure is as described in Example 1; the mass of catalyst is 121 parts, the synthesis gas consists of ethylene glycol (12 parts by weight), air (28.5 parts by volume), and nitrogen (100 parts by volume). Enough trimethyl phosphate is metered into the synthesis gas mixture to make the ratio of the mass of phosphorus to the mass of ethylene glycol 0.1 ppm.

The glyoxal yield is 72.7%, based on the amount of ethylene glycol employed. Formaldehyde is formed to the extent of 0.7%. Combustion to carbon monoxide and dioxide amounts to 14.4%. The yield of the side product glycolaldehyde is 1.8%. After operation for 10 days the glyoxal yield is 73.6%; the yields of formaldehyde, carbon oxides, and glycolaldehyde are 0.6%, 15.3%, and 2.3% respectively.

EXAMPLE 3

Silver-coated steatite spherules 3 mm in diameter (14.5 parts) are so packed in a stainless-steel tube reactor of internal diameter 20 mm that the height of the catalyst filling is 30 cm. A synthesis gas mixture consisting of ethylene glycol (6 parts by weight), air (13.5 parts by volume), and nitrogen (100 parts by volume) is passed through the tube reactor each hour. Phosphorus (0.4 ppm of the mass of ethylene glycol) is added to the synthesis gas in the form of trimethyl phosphate. The reaction temperature is 360° C. The reaction gas is treated as described in Example 1.

The glyoxal yield is 67%, based on the amount of ethylene glycol employed. Formaldehyde, carbon oxides, and glycolaldehyde are formed with yields of 1.0%, 21.4%, and 2.7%. After operation for 7 days the glyoxal yield is 70%; yields of formaldehyde, carbon oxides, and glycolaldehyde are 0.9%. 22.9%, and 1.5% respectively.

EXAMPLE 4 (COMPARISON)

The procedure is a described in Example 1; the mass of catalyst is 115 parts, the synthesis gas consists of ethylene glycol (11.8 parts by weight), air (27 parts by volume), and nitrogen (96.4 parts by volume). Enough trimethyl phosphate is metered into the synthesis gas to make the ratio of the mass of phosphorus to the mass of ethylene glycol 1.5 ppm.

The glyoxal yield is 74%, based on the amount of ethylene glycol employed. Formaldehyde is formed with a yield of 1.0%; carbon oxides are formed with a yield of 18%. After operation for 30 days the glyoxal yield is 71%. The yields of formaldehyde and carbon oxides are 4.3% and 18.5%. After operation for another 330 days the yield of glyoxal is 60%; yields of formaldehyde and carbon oxides are 6.4% and 25%.

We claim:

1. In a process for the preparation of a carbonyl compound of the formula

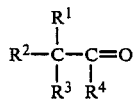
    I wherein $R^1$ is hydrogen, $R^2$ is the group $OR^5$, or $R^1$ and $R^2$ when taken together represent a carbonyl oxygen atom, $R^3$ is hydrogen, alkyl of 1 to 8 carbon atoms or cycloalkyl, $R^4$ is hydrogen or alkyl of 1 to 3 carbon atoms, and $R^5$ is alkyl of 1 to 4 carbon atoms, cycloalkyl or an alkoxyalkyl that may further include a keto or aldehyde oxygen substituent, by oxidizing an alcohol of the formula

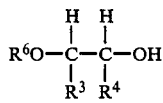
    II wherein $R^3$ and $R^4$ have the same meaning given above and $R^6$ is hydrogen, alkyl or hydroxyalkyl of 1 to 4 carbon atoms, cycloalkyl or alkoxyalkyl that may further carry a hydroxy substituent, said oxidation being carried out in the gas phase at an elevated temperature with an oxygen-containing gas in the presence of a catalyst containing a metal selected from the group consisting of copper, silver and their compounds and alloys, the improvement which comprises:

carrying out the oxidation in the presence of a phosphorus compound that is volatile under the reaction conditions, using a ratio of the mass of the phosphorus to the mass of the alcohol which is less than 0.5 ppm.

2. A process as claimed in claim 1 wherein the ratio of the mass of phosphorus to the mass of the alcohol is 0.05-0.48 ppm.

3. A process as claimed in claim 1 wherein the alcohol of the formula II is one of the compounds of the following formulae:

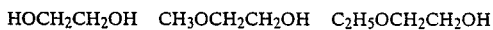

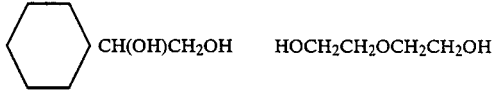

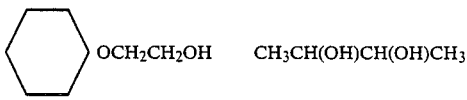

4. A process as claimed in claim 1 wherein glyoxal is prepared from ethylene glycol.

5. A process as claimed in claim 1 wherein oxidation in the gas phase is carried out at temperatures of 225°–500° C.

6. A process as claimed in claim 1 wherein the volatile phosphorus compound is an ester of phosphoric acid, phosphorous acid, or a phosphonic acid.

7. A process as claimed in claim 1 wherein the gas phase reaction is carried out at a temperature of 225°–500° C., and the mass ratio of the phosphorus to the alcohol is 0.05-0.48 ppm.

8. A process as claimed in claim 7 wherein the volatile phosphorus compound is an ester of phosphoric acid, phosphorous acid or a phosphonic acid.

9. A process as claimed in claim 1 wherein the catalyst is metallic copper or silver or a metal alloy containing substantial proportions of copper or nickel.

10. A process as claimed in claim 9 wherein the catalyst is applied to an inert carrier having a specific surface of less than 50 m²/g.

* * * * *